United States Patent
Rishoni

(10) Patent No.: US 10,079,074 B1
(45) Date of Patent: Sep. 18, 2018

(54) SYSTEM FOR MONITORING DISEASE PROGRESSION

(71) Applicant: Prize4Life, Haifa (IL)

(72) Inventor: Shay Rishoni, Ramat Hasharon (IL)

(73) Assignee: PRIZE4LIFE, Haifa (IL)

( * ) Notice: Subject to any disclaimer, the term of this patent is extended or adjusted under 35 U.S.C. 154(b) by 0 days.

(21) Appl. No.: 15/460,529

(22) Filed: Mar. 16, 2017

(51) Int. Cl.
| | |
|---|---|
| *G16H 40/63* | (2018.01) |
| *G06F 19/00* | (2018.01) |
| *G10L 25/48* | (2013.01) |
| *G06F 3/0482* | (2013.01) |
| *G06F 3/0481* | (2013.01) |
| *G06F 3/16* | (2006.01) |
| *G16H 10/60* | (2018.01) |
| *G16H 10/20* | (2018.01) |

(52) U.S. Cl.
CPC .......... *G16H 40/63* (2018.01); *G06F 3/0482* (2013.01); *G06F 3/04817* (2013.01); *G06F 3/167* (2013.01); *G06F 19/322* (2013.01); *G06F 19/3406* (2013.01); *G06F 19/3418* (2013.01); *G06F 19/3481* (2013.01); *G10L 25/48* (2013.01); *G16H 10/60* (2018.01); *G06F 19/363* (2013.01); *G16H 10/20* (2018.01)

(58) Field of Classification Search
CPC .............. G06F 19/3406; G06F 19/3418; G06F 19/3481; G06F 19/363; G06F 3/04817; G06F 3/0482; G06F 3/167; G01L 25/48
USPC ....................................................... 705/2, 3
See application file for complete search history.

(56) References Cited

U.S. PATENT DOCUMENTS

| | | | | |
|---|---|---|---|---|
| 2010/0169409 A1* | 7/2010 | Fallon | ................. | G06F 19/3418 709/203 |
| 2010/0217157 A1* | 8/2010 | Tasch | ................... | A61B 5/1038 600/592 |
| 2010/0234693 A1* | 9/2010 | Srinivasan | ............ | A61B 5/1118 600/300 |
| 2016/0345908 A1* | 12/2016 | Samzelius | ........... | G06F 19/3487 |

OTHER PUBLICATIONS

Cedarbaum et al., "The ALSFRS-R: a revised ALS functional rating scale that incorporates assessments of respiratory function" Journal of the Neurological Sciences 169:13-21 (1999).

* cited by examiner

*Primary Examiner* — Eliza Anne Lam

(74) *Attorney, Agent, or Firm* — Browdy and Neimark, PLLC

(57) ABSTRACT

Personal communication devices and computer-implemented systems for monitoring of ALS disease state of a patient are presented. The computer-implemented system comprises assignment selection module configured to access a library comprising predefined activity(ies), and enable selection of at least one predefined activity to be monitored by sensor(s) associated with the patient; assignment execution module configured to identify sensing signal(s) from the sensor(s) and generate corresponding output signal(s) indicative of the predefined activity, the sensing signal(s) comprising at least one of the following: reading, drawing, finger tapping, speaking, breathing, walking; and assignment reporting module configured to communicate with a data analyzer for communicating the output signal(s) indicative of the predefined activity to the data analyzer, thereby enabling storing the output data in a memory for use in monitoring and analyzing the ALS disease state of the patient.

7 Claims, 3 Drawing Sheets

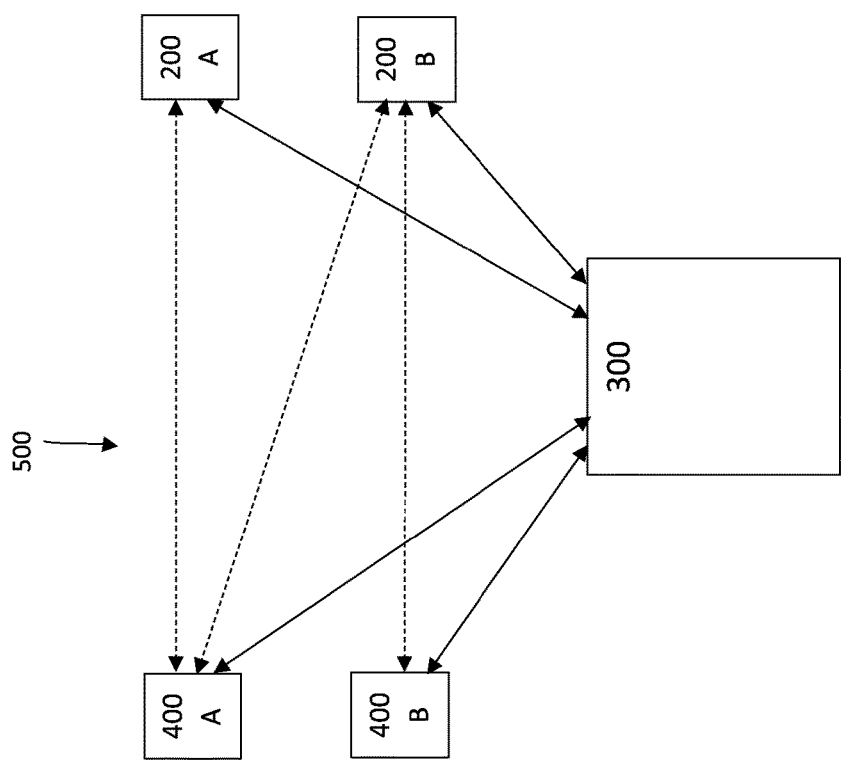

SYSTEM FOR MONITORING DISEASE PROGRESSION

TECHNOLOGICAL FIELD AND BACKGROUND

The present invention is in the field of healthcare applications, and relates to a system and method for monitoring disease severity and progression, in particular Amyotrophic Lateral Sclerosis (ALS) disease.

ALS is a progressive neurodegenerative disease that affects nerve cells in the brain and the spinal cord. The progressive degeneration of the motor neurons, which reach and activate the muscles throughout the body, eventually leads to their demise. When the motor neurons die, the ability of the brain to initiate and control muscle movement is lost. With voluntary muscle action progressively affected, patients gradually lose their ability to speak, eat, move and breathe.

There are two different causes for ALS, sporadic and familial. Sporadic, which is the most common form of the disease, may affect anyone, anywhere. Familial ALS, which is inherited, accounts for 5 to 10 percent of all cases. In familial ALS, there is a 50% chance each offspring will inherit the mutated gene and develop the disease.

The gold standard assay to monitor disease progression is a subjective questionnaire, designated ALSFRS (ALS Functional Rating Scale), The questionnaire is answered by the patient and/or his doctor during routine examination, usually once in 3 months.

While scientists are making progress in exploring the disease causes and molecular mechanism, no cure for ALS is known to date. The average survival from onset to death is three to five years. Only about 10% of the patients survive longer than years. The only FDA-approved medication, Riluzole, may slow disease progression and extend life expectancy by several months in some patients.

GENERAL DESCRIPTION

The present invention provides a novel system that will revolutionize ALS monitoring by switching from in-clinic monitoring by an ALS professional to personal monitoring by ALS patients and recording of minute details from a patient's daily activities. This easy-to-use home-based tool will allow reliable and frequent subject monitoring to supplement clinical visits. The invention will allow clinics to conduct a close and objective follow up of their patients, and the system will generate alerts when life-saving interventions are required. The present invention defines the types of information to be gathered from the patients, in the most effective, convenient means of collecting the data. Thus, the invention provides a digital biomarker for disease progression. Additionally, the present invention provides a mechanism which alerts about any deterioration in the ALS patient's health and enables prompt professional intervention when required.

This may be achieved by real-time following after ALS disease progression in ALS patients, including the majority of the patients who typically stay at home in their natural environment, to enable better monitoring disease severity and its progression.

Furthermore, the present invention makes all future clinical trials cheaper in millions of dollars (the average cost for a large Phase III clinical trial is $26 million), by removing the barriers of patients' recruitment and retention, simplifying patients monitoring and shortening trial times, as well as gaining a deeper, more accurate and objective understanding of the disease progression and the way it is effected by specific medications.

The present invention provides systems and methods for building a comprehensive and objective database which includes, inter alia, objectively-collected data indicative of ALS disease's various symptoms, physical activities and/or abilities in ALS patients which are affected by the disease, as well as comparative data of healthy people as a control group. The database promotes creation of an objective measure (both qualitative and quantitative measure) of ALS disease evaluation and performance of high-level of data analysis based on novel algorithms, the analyzed data will be used in disease diagnosis, in personalized monitoring of the disease progression, and in prediction of future stages of the disease progression in an individual as well as the patient's life expectancy. Being a cheaper, accessible and more accurate, the invention will advance ALS research and ultimately shorten the path to finding a cure for the disease.

To this end, the invention provides a system (platform) for collecting and analyzing data from end users, ALS patients as well as healthy people, and storing the data, such as in a single collective repository, to be accessed and used for monitoring of disease progression, evaluation and analysis, and for treatment development. The invention provides various algorithms for data analysis which output indicates a stage of the disease and quality of life of the patient.

The system may run, as an application, on a single communication device kept with an ALS patient or a control (e.g., healthy) person. In this case, the device includes or communicates with at least one sensor, possibly located in the device, which provides sensing signals in response to an assignment performed by a user, or sensing signals provided passively by a sensor which monitors the user's activity.

The system may be utilized in a server-client environment enabling for collecting data passively or actively from the end users (the client side) and saving the collected data into a memory in the server and/or the client. Typically, the client runs on a computer, such as a hand-held device configured to be kept with and used by the patient or the healthy person, e.g. a Smartphone. The client may be implemented via an application that runs on the hand-held device.

In the different scenarios of data collection, the system, at the user end, uses variety of technologies separately or collectively to collect the data. For example, the system utilizes location based technologies such as GPS, mobility sensors such as accelerometer and/or barometer. The system may also utilize an image or video sensor, e.g. a camera, for acquiring images/videos for various tasks. The system may also utilize sensors for measuring medical data such as body temperature, and/or environmental conditions (temperature, humidity, pressure, etc.).

The monitored tasks may include active as well as passive (in the background) activities.

According to the invention, the tasks presented to a specific person/ALS patient, their kind, level and repetition may be individualized based on the patient's historical collected data and the analysis thereof.

Additionally, according to the invention, the system which monitors and collects the data is dynamic and has a self-learning algorithm, such that it controls and/or adjusts the sensor(s) involved in the undertaken task, based on the analysis of the previous task(s), so as to improve the monitoring between successive relevant tasks.

Accordingly, the invention provides system and method which automatically and autonomously as well as actively provide a link, e.g. a correlation, between various physical or behavioral data and a disease condition/state. The system receives as an input the various physical or behavioral data, integrates the plurality of data received and generates as an output data indicative of ALS disease progression state. The technique of the invention thereby provides a digital biomarker for assessing disease severity and progression in the patient.

Thus, according to one broad aspect of the invention, there is provided a computer-implemented system for monitoring ALS disease state of a patient. The system comprises: assignment selection module configured to access a library comprising a plurality of predefined activities, and enable selection of at least one predefined activity of said plurality of predefined activities to be monitored by one or more predetermined sensors associated with the patient; assignment execution module configured to identify one or more sensing signals from said one or more sensors and generate corresponding one or more output signals indicative of said at least one predefined activity, said one or more sensing signals comprising at least one of the following: reading, drawing, finger tapping, speaking, breathing, walking; and assignment reporting module connected to said assignment execution module and configured to communicate with a data analyzer for communicating said output signal indicative of said at least one predefined activity to the data analyzer, thereby enabling storing said output data in a memory for use in monitoring and analyzing the ALS disease state of said patient.

In some embodiments, the assignment selection module comprises a graphical user interface configured for providing display data for displaying each of said plurality of predefined activities as a dedicated icon enabling said selection of the at least one predefined activity via icon selection on a display.

In some embodiments, the assignment selection module comprises an audio voice interface configured for presenting each of said plurality of predefined activities as a dedicated audio signal enabling said selection of the at least one predefined activity via corresponding audio or data entry.

In some embodiments, the sensing signals indicative of the reading activity comprise location data about the patient's finger position with respect to a sensing surface, being indicative of patient's selection on said sensing surface.

In some embodiments, the sensing signals indicative of the drawing activity comprise location data about the patient's finger movement along a sensing surface.

In some embodiments, the sensing signals indicative of the speaking activity comprise one or more parameters of detected audio signals, said one or more parameters comprise at least one of the following: intensity of the audio signals, a time pattern of detection of the audio signals, a degree of accuracy of the detected audio signals, and breathing cycle.

In some embodiments, the assignment execution module comprises a voice recognition module for processing and analyzing the audio signals and determining said degree of accuracy of the audio signals.

In some embodiments, the sensing signals indicative of said at least one predetermined activity comprise a time pattern of the sensing signals being detected.

In some embodiments, the sensing signals indicative of the walking activity comprise acceleration data.

In some embodiments, the sensing signals indicative of the walking activity comprise location and time data.

In some embodiments, the sensing signals indicative of the walking activity comprise altitude data.

In some embodiments, the assignment reporting module comprises a processor utility comprising said data analyzer being configured to analyze said sensing signals and generate analysis results. The analysis results may comprise personal statistics of a patient as compared with an average of a plurality of users.

In some embodiments, the assignment reporting module is configured for communication with the data analyzer via a communication network, for transmitting to the data analyzer said output signal indicative of said at least one predefined activity, and for receiving data indicative of analysis results.

According to another broad aspect of the invention, it provides a computer readable medium including one or more sequences of instructions for monitoring ALS disease state of a patient, wherein execution of the one or more sequences of instructions by one or more processors of a mobile computing device causes the mobile computing device to perform the following process:

accessing a library comprising a plurality of predefined activities, and selecting of at least one predefined activity of said plurality of predefined activities to be monitored by one or more predetermined sensors associated with the patient;

identifying one or more sensing signals from said one or more sensors and generating corresponding one or more output signals indicative of said at least one predefined activity, said one or more sensing signals comprising at least one of the following: reading, drawing, finger tapping, speaking, breathing, walking; and communicating with a data analyzer for communicating said output signal indicative of said at least one predefined activity to the data analyzer, thereby enabling storing said output data in a memory for use in monitoring and analyzing the ALS disease state of said patient.

The invention, in yet a further broad aspect, provides a personal communication device configured for positioning in a vicinity of an ALS disease patient, the device comprising: a user interface utility; a memory utility; a communication utility for communication with remote system via a communication network; a sensor assembly comprising a plurality of sensors comprising at least the following sensors: a proximity sensor; audio sensor; image sensor; location sensor; motion sensor; and a data processing utility preprogrammed for running a software application configured for monitoring ALS disease conditions state of a patient, said software application comprising:

assignment selection module configured to access a library comprising a plurality of predefined activities, and enable selection of at least one predefined activity of said plurality of predefined activities to be monitored by said sensor assembly;

assignment execution module configured to identify one or more sensing signals from said sensor assembly and generate corresponding one or more output signals indicative of said at least one predefined activity, said one or more sensing signals comprising at least one of the following: reading, drawing, finger tapping, speaking, breathing, walking activity; and assignment reporting module connected to said assignment execution module and configured to communicate with a data analyzer for communicating said output signal indicative of said at least one predefined activity to the data analyzer, thereby enabling storing said output data in a memory for use in monitoring and analyzing the ALS disease conditions state of said patient.

In some embodiments, the personal communication device is configured as a smartphone device.

In some embodiments, the personal communication device comprises a touch screen device comprising said proximity sensor.

In some embodiments, the personal communication device comprises at least one integrated camera, a microphone assembly, and a speaker assembly.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 3 illustrates a non-limiting example of a plurality of devices utilizing the system of the present invention.

DETAILED DESCRIPTION OF EMBODIMENTS

The present invention discloses, in one of its aspects, a computer-implemented system for use in monitoring ALS disease progression in ALS patients. The computer-implemented system can be a software/application product interface that runs on a computing device, such as a personal computer, a personal communication device, a smartphone or a dedicated hardware. The system utilizes sensing data which is provided by one or more sensors associated with an individual using the hardware on which the system of the invention runs. The sensor(s) generate(s) the sensing data based on an input from the individual (actively or passively) during performing or monitoring of a task or assignment related to the ALS disease. Such one or more sensors can typically be gathered together in one device or can alternatively be implemented separately while communicating with the system of the invention. Advantageously, the system of the invention can be run on a smartphone, which typically includes sensors and which is portable and readily available.

Figure 1:
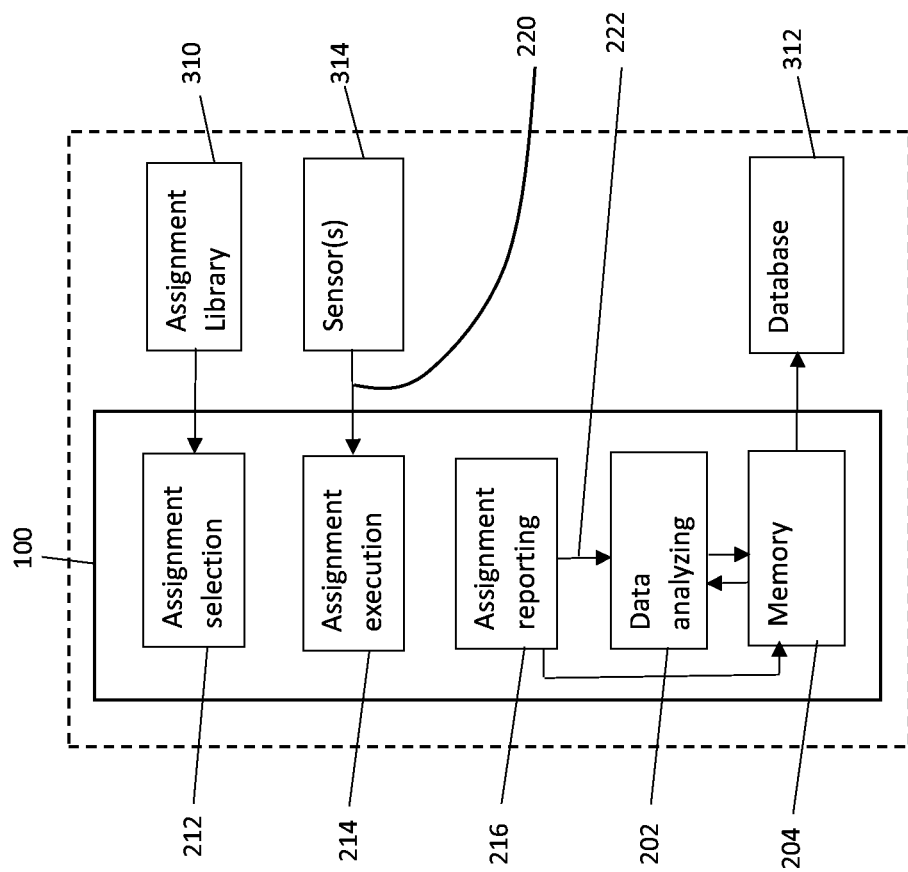
FIG. 1 illustrates one non-limiting example of a system according to the invention.

Reference is made to FIG. 1 illustrating a non-limiting example of a system 100 configured according to the invention. The system 100, which is a software program interfacing with a suitable hardware (a computer, a smartphone, . . . ), includes an assignment selection module 212, an assignment execution module 214, an assignment reporting module 216, a data analyzing module 202 and a memory 204. According to the invention, the mentioned modules are configured to communicate with various other modules or utilities, such as a library 310 containing assignments, one or more sensors 314 and a database 312. The library 310, the sensor(s) 314 and the database 312 are not necessarily part of the system 100, however they can be part of a single device utilizing the invention as illustrated by the dashed line, such device can be a smartphone; alternatively, they can be implemented in more than one device, as will be further exemplified below.

The assignment selection module 212 is configured to access the assignment library 310 which includes a plurality of predefined activities, as will be detailed further below. The assignment selection module 212 is further configured to enable selection of at least one predefined activity of the plurality of predefined activities to be monitored by one or more predetermined sensors 314.

In one specific example, the selection of the assignment/task is enabled via selecting an icon on a display. In such case, the assignment selection module 212 comprises a graphical user interface configured for providing display data for displaying each of the plurality of predefined activities as a dedicated on the display.

The assignment execution module 214 is configured to identify one or more sensing signals 220 from the one or more sensors 314 and generate corresponding one or more output signals 222 indicative of the at least one predefined activities included in the library 310. The one or more sensing signals 220 may relate to at least one of the following: reading, drawing, finger tapping, speaking, breathing, and walking. These, as will be further exemplified below, are activities being indicative of the ALS disease condition or stage. The sensing signals 220 can include, inter alia, location or space data, time data, frequency data and medical data (such as heart pulse, temperature, . . . ).

The assignment reporting module 216 is configured to communicate with a data analyzing module 202 for communicating the output signal indicative of the at least one predefined activity to the data analyzing module 202, thereby enabling storing the output data in a memory 204 for use in monitoring and analyzing the ALS disease condition. Alternatively, the assignment reporting module 216 communicates with the memory 204 that stores the output signal which is then sent to the data analyzing module 202. Preferably, the output data is further stored or transferred to the database 312, which may be a local or a distant (e.g. cloud) storage. To this end, the monitoring system 100 is configured for building a database and/or utilizing previously created database. For creation of such database, and possibly also periodically improving it, the system of the invention may be used for monitoring similar ALS related conditions/symptoms in non-ALS patients, functioning as a control group.

The various tasks are related to examination of ALS symptoms or side effects or conditions. The user performs the task while a suitable sensor 314 records the user's activity/input. For example, the task may be asking the user to record a sentence conveyed to him (such as through a display or a speaker), while an audio sensor, such as a microphone, captures the user's voice. The data indicative of the user's input is then saved to the memory 204, thus serving as a step for building the database 312 to be used in ALS research.

Specific non limiting examples of the tasks which may be included in the library 310 are as follow:

Reading:

Reading and answering questions listed in a questionnaire (Standard ALSFRS questions (Cedarbaum 1999)).

Speaking:

Recording prescribed sentences. For example, recording repetition of a sentence. Some other speaking tasks include sentences that were particularly designed for detection of difficulty or deterioration in speech in ALS patients. In one aspect, the sentences contain consonants, classifiable to ALS, for which pronunciation is deleterious. In another aspect, the sentences diagnose consistent features of speech deterioration in ALS patients. For example, the speech task can include a certain paragraph which reading rate is reduced even in early development of ALS speech deterioration. In another example, the sentence contains motions in which distinct changes in the rate and in the regularity of the sequence occur with the progress of ALS speech deterioration. The sentences can be designed for diagnosis of dysdiadochokinesia, by checking the alternate motion rate (AMR) and synchronized motion rate (SMR) relative timing of speech.

Fine Motor Skills:

Tracing shapes with the finger. Examples of shape may include straight as well as curved lines.

Finger tapping tasks.

Breathing:

Recording voices indicative of breathing cycle, such as recording longest "ahhhhhh" sound, or counting slowly.

Walking:

Walk short or very short distances, while a mobility sensor is carried by the user (e.g., placed in waist area).

Salivation:

Recording audio.

Swallowing:

Recording and analysing audio to detect choking. Taking photos of food items for next meal. Saving the time taken for a meal from start to end.

Cutting Food:

Taking photos of the table before and after.

Dressing and Hygiene:

Taking photos of cloths the user is planning to wear and recording time taken for dressing up.

Climbing Stairs:

Audio, mobility sensing and recording when a user starts climbing stairs.

In all the above examples, after the user chooses a task to perform, the relevant sensor is activated in order to sense the relevant signal coming from the user. For example, during the speaking task, a microphone is activated in order to record the voices.

The above described tasks are active tasks which require the user's action, to choose and perform the task. Additionally, the system of the invention is also capable of running passive tasks in the background and collecting respective data. In this case, no intervention is required from the user and the tasks are executed according to algorithms running independently. The algorithms control the time on which the specific task starts or stops and duration of the task. The different tasks are monitored directly by the relevant sensor (s).

Examples of the passive tasks include, inter alia, the following:

Speaking:

monitoring call log to learn user preferences with regards to phone calls: incoming vs. outgoing calls, length of calls, preferences to speak vs. writing messages.

Writing/Fine Motor Skills:

monitoring message log to learn user preferences with regard to writing messages (as an indication to fine motor skills): number of messages, number of characters per message, number of corrections, preferences to write messages vs. make phone calls.

Breathing:

Audio recording during walk and speech.

Walking:

Using sensors, such as accelerometer and GPS system to estimate walking patterns, the number of steps taken and distances passed.

Swallowing:

Recording audio automatically without intervention from the user.

Climbing Stairs:

Using log data from sensors such as accelerometer and barometer

Turning in Bed:

Audio recording and accelerometer inputs when device 200 is placed on the bed while the user is asleep.

Orthopnea:

Audio recording and analysis when phone is close to the user during night time.

It should be noted that the library 310 is dynamic, such that the tasks (the active tasks chosen actively by the user) can be updated as needed. The update process may be totally voluntary or may be dependent on the recorded input data from users. In other words, the system 100 includes a self-learning algorithm configured to update the tasks according to the analysis made to the data accumulated. Moreover, the system can control the sensor(s) and adjust the sensor(s) properties, such as its sensitivity to different physical activities, in order to improve the monitoring procedure.

The sensor(s) 314 include(s) one or more of the following sensors: touch/proximity sensor (e.g. a touch screen or a sensing surface), accelerometer, barometer, location sensor (GPS), audio sensor (microphone), image sensor (camera). Each task may utilize more than one sensor simultaneously or successively.

The passive tasks, which examples of them are mentioned above, are typically run in the background according to predetermined regimes executed by the processing utility 202. The regimes define the schedule, duration, recurrence of each task.

Examples of the sensing signals 220 generated by the sensors 314, with respect to the various assignments and sensors used in each assignment include:

In the case of a drawing activity, the sensing signals can include location and time data about the patient's finger movement along a sensing surface.

In the case of a speaking activity, the sensing signals can include one or more parameters of detected audio signals, the one or more parameters can be the intensity/amplitude of the audio signals, a time pattern of detection of the audio signals (e.g. the rate in which a specific sentence is spoken being indicative of ALS condition), a degree of accuracy of the detected audio signals (e.g. detection of pronunciation of specific consonants), and breathing cycle.

In the case of a walking activity, the sensing signals can include acceleration data, location and time data and/or altitude data.

The system 100 is capable of generating a qualitative output indicative of the medical state of the user, based on the quantitative data recorded by the sensor(s) 314 and saved in the database 312 and/or the memory 204. The data analyzing module 202 is configured to continually process and analyze the data of the variety of tasks accumulated in the memory 204/database 312. The processing is done for each task alone and for a plurality of tasks together. Processing and analysis of each task alone tracks any deterioration in the user's examined ability and may adjust the task as necessary. When more than one task are involved, the processing and analysis tracks deterioration of one ability or related abilities. The processing of the quantitative data accumulated in the memory 204/database 312 enables generation of a qualitative decision about the medical state of the user/patient presenting a digital biomarker for assessing disease severity and progression. The system may then alert about any deterioration in a specific ability (speaking, breathing, etc.) or overall medical state indicative of the disease progression. The system can also predict, based on sufficient accumulated data for a user and flowing development of algorithms based on the data, the stage and rate in which the disease is progressing in its different aspects.

Figure 2:
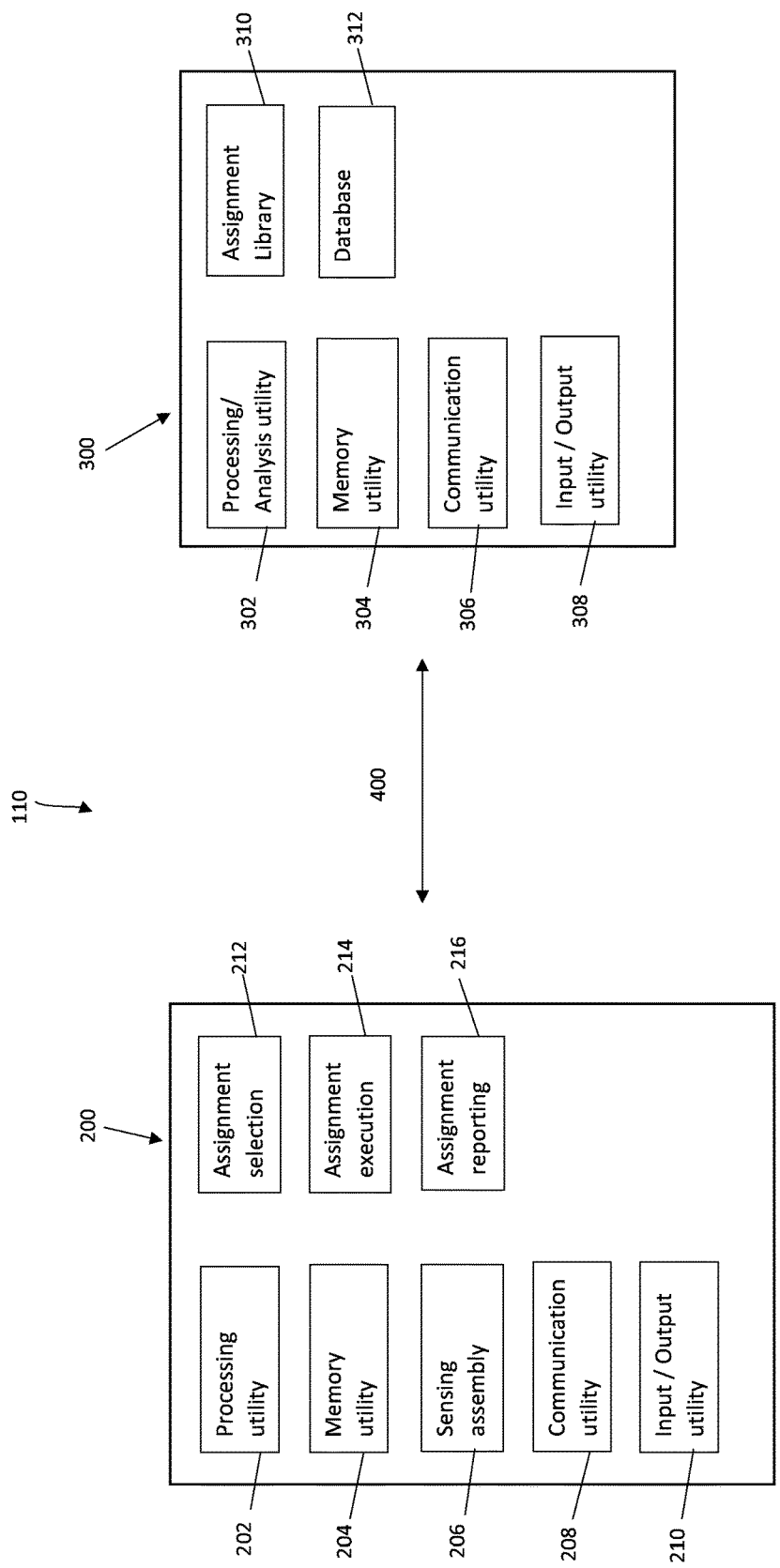
FIG. 2 illustrates another non-limiting example of a system according to the invention.

As described above, the system 100 may be totally implemented as an independent application running on a computing device, e.g. a smartphone, or its modules may be distributed between more than one device. specifically, the data analyzing module may be located in a second device, such that the output data generated by the assignment reporting module 216 is conveyed/transmitted to the second device to perform on it analysis. One non-limiting example is illustrated in FIG. 2. Shown in the figure is a system 110 in accordance with the present invention, utilizing the modules of the system 100, for use in monitoring of ALS disease progression in ALS patients.

The system 110 includes a device 200 functioning as a client and a device 300 functioning as a server in a client-server environment. Both devices 200 and 300 are configured for communicating with each other in a bi-directional communication link 400, which may be wired or wireless, through suitable and known in the art communication utilities 208 and 306 in the devices 200 and 300 respectively. The device 200 is kept with an end user, who may be an ALS patient or a healthy person functioning as a control group, and is used for presenting to the user various tasks and for receiving through a suitable interface an input from the user. In a non-limiting example, the device 200 can be a handheld mobile phone, e.g. a smartphone. As illustrated in the figure, the device 200 includes utilities such as a processing utility 202, a memory utility 204, the above-mentioned communication utility 208 and an input/output utility 210 configured to receive and send through the user and/or the communication utility 208 various data as will be further described below.

The device 300 can be a physical single server, a network including a plurality of servers or a cloud-based server.

Accordingly, generally, the system 110 enables a user using the device 200 to access and choose one predetermined activity or task from a plurality of tasks stored in the library 310, which may be implemented in the device 200 and/or the device 300 as shown in the figure, or may be alternatively saved in a cloud storage environment (not shown).

The device 200 also includes the assignment selection module 212, the assignment execution module 214 and the assignment reporting module 216, which functions are described above. The assignment reporting module 216 is configured to communicate with either the processing utility 202 located in device 200, or with the data analysis utility 302 located in the server 300, for communicating the output signal indicative of the at least one predefined activity to the processing utility 202/data analysis utility 302, thereby enabling storing the output data in a memory utility (204 or 304) for use in monitoring and analyzing the ALS disease condition.

The data processing utilizing algorithms of the invention may be done in either the processing utility 202 or the processing utility 302, or it may be distributed between them, such that specific analysis is done in each. For example, processing the output data by comparing it to a previously collected data from the same user can be done locally in processing utility 202, which then generates a subsequent corresponding task to follow the progression of the specifically monitored ALS disease condition in that user. Alternatively, in order to compare the output data from one user with the output data from other users and generate the subsequent task based on the collective data from plurality of users, the processing may be done at the processing utility 302.

The processing and analyzing utilities 202 and or 302 can perform various analysis on the data provided to them by employing different algorithms according to the invention.

The analyzing algorithms of the invention, by utilizing one or more of the output data 222, can provide, inter alia: individual data features in fine motor skills, finger tapping, speech, breathing and walking data which can be indicative of disease progression (as compared to questionnaire self-assessment and/or to the clinic-based data); creation of a digital phenotype (or signature) of a patient at each time-point of disease progression; creation of a new objective measure of ALS disease progression; identification of combined data features that can predict disease progression such as decrease of lung function.

The sensing assembly 206 is located in the device 200 (the smartphone) and, as described, includes one or more of the following sensors: touch/proximity sensor (e.g. in the form of a touch display), accelerometer, barometer, location sensor (e.g., GPS), audio sensor (e.g., microphone), image sensor (e.g., camera). Each task may utilize more than one sensor simultaneously or successively.

In one embodiment, the system may include an alert system which connects between a user and his physician by generating and sending alerts to the physician whenever a deterioration in the patient's status occurs, thus enabling close tracking and prompt intervention when needed.

Reference is made to FIG. 3, illustrating a non-limiting example of an alert mechanism embedded in a system of the present invention. The system 500 includes the device/server 300, a plurality of device 200 and a plurality of device 400, two devices from each are exemplified in the figure, 200A, 200B, 400A, 400B. The devices 400A and 400B are communication devices kept with two respective medical professionals, e.g. physicians, and are configured for communicating with the devices 300 and/or 200. Typically, devices 400A and 400B are smartphones loaded with a specific program module that enables receiving/sending information, such as alerts about medical deterioration, from/to device 300 and/or devices 200A and 200B. This way, the medical professional can keep continuous track of their ALS patients, and can be alerted of any deterioration in any of the ALS conditions monitored by the system of the invention. as shown in the bob-limiting example of FIG. 3, user 200A is connected with the medical professional 400A, directly and/or indirectly through the server 300. In addition, user 200B is connected to both medical professionals 400A and 400B. in the latter case, user 200A can be fully monitored simultaneously by medical professionals 400A and 400B, or he can be monitored partially with respect to specific ALS conditions by each of the medical professionals.

The invention claimed is:

1. A personal communication device configured for positioning in a vicinity of an Amyotrophic Lateral Sclerosis disease patient, the device comprising:
    a user interface utility;
    a memory utility;
    a communication utility configured and operable for communication with a second communication utility in a remote system via a communication network;
    a sensor assembly comprising a plurality of sensors comprising at least the following sensors: a proximity sensor; audio sensor; image sensor; location sensor; motion sensor; and a data processing utility preprogrammed for running a software application configured for monitoring ALS disease state of a patient, said software application comprising:
    assignment library comprising a plurality of predefined activities, performance of which is indicative of the ALS disease's condition or stage, the predefined activities comprising active tasks that require active selection and input from a user and passive tasks that run in background according to a predetermined regime, the predefined activities comprising reading, drawing, speaking, breathing, and walking activities;

assignment selection module comprising a user interface configured to access said assignment library and present at least some of the predefined activities from the assignment library to the patient to enable the patient's selection of at least one of the predefined activities to thereby activate monitoring of the patient active performance of the selected at least one active task and monitoring of the at least one passive task running in the background by one or more sensors of a plurality of predetermined sensors associated with the patient;

assignment execution module configured to be responsive to receive sensing signals during said at least one activated predefined activity from said one or more sensors during said at least one predefined activity and to generate corresponding one or more output signals indicative of said at least one activated predefined activity; and assignment reporting module connected to said assignment execution module and configured to receive the one or more output signals indicative of said at least one activated predefined activity and communicate with a data analyzer for transmitting said one or more output signal indicative of said at least one predefined activity to the data analyzer, thereby enabling analyzing said one or more output signals indicative of said at least one activated predefined activity and storing analysis results in a memory for use in monitoring and analyzing the ALS disease state of said patient.

2. The personal communication device according to claim 1, configured as a smartphone device.

3. The personal communication device according to claim 1, comprising a touch screen device comprising said proximity sensor.

4. The personal communication device according to 1, comprising at least one integrated camera, a microphone assembly, and a speaker assembly.

5. The personal communication device according to claim 1, wherein said assignment execution module comprises a voice recognition module configured for analyzing detected audio signals and determining a degree of speech accuracy or breathing pattern.

6. The system according to claim 1, wherein said input data indicative of sensing signals is received from a plurality of ALS patients.

7. The system according to claim 1, wherein said ALS disease state comprises one or more of the following: disease stage, disease progression speed, and lifetime expectancy.

* * * * *